United States Patent [19]

Captain

[11] 4,098,121
[45] Jul. 4, 1978

[54] HUMIDITY INDICATOR

[75] Inventor: Khushroo M. Captain, Cambridge, Mass.

[73] Assignee: Foster-Miller Associates, Inc., Waltham, Mass.

[21] Appl. No.: 786,006

[22] Filed: Apr. 8, 1977

[51] Int. Cl.² .......................................... G01N 19/10
[52] U.S. Cl. ..................................................... 73/337
[58] Field of Search ................... 73/300, 335, 337, 406

[56] References Cited

U.S. PATENT DOCUMENTS

| 2,542,414 | 2/1951 | Jansen | 73/406 X |
| 3,204,872 | 9/1965 | Whear | 73/337 X |

Primary Examiner—R. C. Queisser
Assistant Examiner—John S. Appleman

Attorney, Agent, or Firm—Morse, Altman, Oates & Bello

[57] ABSTRACT

A humidity indicator with a housing having mounted therein a sensing element that changes dimensionally in response to humidity variations. A flexible diaphragm is captively held within the housing and is moved by dimensional changes of the sensing element. An intermediate plate with a cavity forms a reservoir on the flexible diaphragm for a transduction fluid. An adjustable member received within the sensing element contacts a portion of the flexible diaphragm bounding the reservoir for initial calibration of the humidity indicator. A dial and cover assemblage having an internal capillary groove is mounted on the intermediate plate, a port interconnecting the reservoir and capillary groove. The transduction fluid within the reservoir flows into the capillary groove and provides an indication of the percent of relative humidity.

10 Claims, 3 Drawing Figures

HUMIDITY INDICATOR

BACKGROUND OF THE INVENTION

1. Field of the Invention

The present invention relates to indicating devices and, more particularly, is directed towards humidity indicators.

2. Description of the Prior Art

Humidity indicators of various configurations have been introduced with varying degrees of success. A humidity indicator utilizing a polyamide resin sensing element which cooperates with a flexible diaphragm in displacing a tranduction fluid constrained within a capillary tube is disclosed in a final report entitled "Development Of A Low-Cost Humidity Indicator For Packaging." The humidity indicator configuration described therein requires that a barrier liquid and a transduction liquid be filled sequentially through a single orifice which could result in entrained bubbles. A sliding seal, which is prone to leakage under pressure, is provided for a calibration screw which projects into and acts directly on a reservoir containing the transduction fluid. An adhesive bond that is provided between the sensing element and diaphragm tends to separate partially and degrades instrument accuracy. In high humidity environments, i.e. greater than 70% relative humidity, the barrier liquid overflows into the housing and does not retract uniformly within the capillary tube when the humidity decreases. In consequence, bubbles and voids formed in the barrier liquid enter the transduction fluid and cause a breakup of the capillary column. A need has arisen for improvements in humidity indicating devices.

SUMMARY OF THE INVENTION

It is an object of the present invention to provide a humidity indicator which does not suffer from the heretofore mentioned disadvantages. The humidity indicator embodying the present invention includes a housing having mounted therein a sensing element that changes dimensionally in response to humidity variations. A flexible diaphragm, which is captively held within the housing in contact with the sensing element and is moved by dimensional changes of the sensing element, constitutes a common wall between the sensing element and a reservoir formed by an intermediate plate. A cover and dial plate assemblage formed with a capillary groove containing a barrier fluid is fastened to the housing in superposition with the intermediate plate. A transduction fluid within the reservoir is constrained to flow within the capillary groove in response to movement of the diaphragm due to humidity variations. An adjusting member is turned into the sensing element and contacts the flexible diaphragm for initial calibration of the humidity indicator. Displacement of the transduction fluid within the reservoir chamber due to volume changes in the reservoir which results from dimensional changes of the sensing element causes the transduction fluid to flow within the capillary groove. The interface of the transduction and barrier fluid provides an indication of the percent of relative humidity.

Other objects of the present invention will in part be obvious and will in part appear hereinafter.

The invention accordingly comprises the apparatuses and systems, together with their parts, elements and interrelationships that are exemplified in the following disclosure, the scope of which will be indicated in the appended claims.

BRIEF DESCRIPTION OF THE DRAWINGS

A fuller understanding of the nature and object of the present invention will become apparent upon consideration of the following detailed description taken in connection with the accompanying drawings, wherein.

DETAILED DESCRIPTION OF THE PREFERRED EMBODIMENTS

Figure 1:
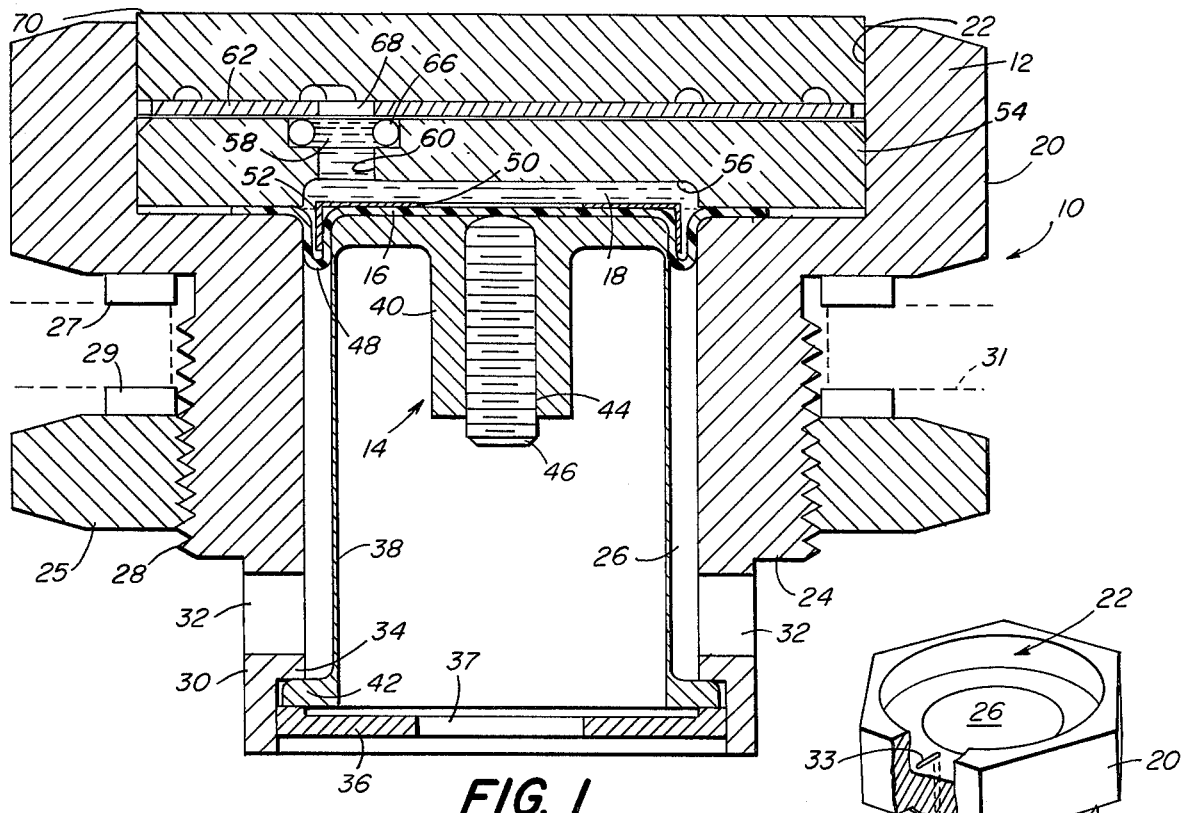
FIG. 1 is a sectional view in side elevation of a humidity indicating device embodying the invention.
Figure 2:
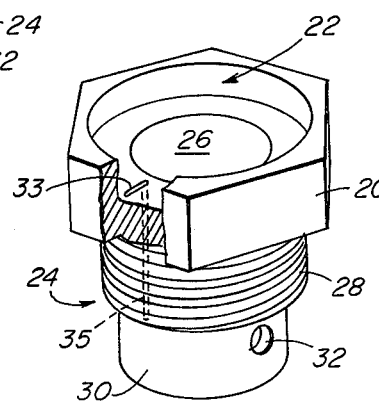
FIG. 2 is a perspective view of the housing of FIG. 1.

Referring now to the drawings, a humidity indicator 10 embodying the present invention comprises a housing 12, a sensing element 14, a flexible diaphragm 16 and a transduction fluid 18. Housing 12 is composed of a plastic which exhibits very low moisture absorbing characteristics such as a plastic derived from acrylonitrile, butadiene and styrene, commonly known as ABS. Housing 12 includes an enlarged head 20 having a central cavity 22 and a cylindrical body 24 which is formed with a central bore 26. As shown in FIG. 1, cavity 22 and bore 26 constitute a substantially T-shaped opening. Body 24 is provided with an upper threaded portion 28 and a lower narrowed portion 30 having a pair of ports 32. A nut 25 and a pair of elastomeric gaskets 27, 29 are provided for fastening humidity indicator 10 to a panel 31, for example a container wall. A trough 33 formed in the floor of cavity 22 communicates with a vent hole 35 that extends longitudinally from the trough to the bottom of threaded portion 28. At the lower margin of body 24, bore 26 is somewhat enlarged to form a step 34 that is configured to captively hold sensing element 14 in conjunction with a retainer 36.

Sensing element 14 includes a thin walled cylindrical body 38 having a head 40 at an upper portion and an outwardly extending flange 42 at a lower portion. Sensing element is composed of a plastic which exhibits high sensitivity to humidity and changes dimensionally in response to humidity variations. In the illustrated embodiment, sensing element 14 is composed of a plastic such as the reaction product of hexamethylene and adipic acid which is sold by E. I. duPont under the trade name nylon 6/6. In an alternate embodiment, sensing element 14 is composed of cellulose propionate. Sensing element 14, which is approximately one inch long, is configured to be loosely received within bore 26 with flange 42 engaging step 34. Retainer 36, for example a disc having a central opening 37, is pressed into the enlarged section of bore 26 for securing sensing element 14. Preferably, retainer 36 is fastened using a suitable bonding agent. The wall thickness of body 38 is in the range of 2 to 3 mils. Head 40, which has a substantially T-shaped profile in cross section, is provided with a central internally threaded hole 44 that is configured to receive a threaded adjusting member 46. Access to adjusting member 46 is provided through central opening 37. As shown in FIG. 1, adjusting member 46, for example a polyamide resin screw, is turned into hole 44 in contact with flexible diaphragm 16 for initial calibration of humidity indicator 10.

Flexible diaphragm 16, which is composed of a reinforced elastomeric such as polyester reinforced buna N rubber, is a disc shaped member that is approximately 0.02 inches in thickness and is formed with an intermediate annular U-shaped flange 48. The diameter of flexible diaphragm 16 is approximately 1.5 inches and the diameter of annular flange 48 is approximately 0.75 inches. The margins of diaphragm 16 rest on the floor of cavity 22 and flange 48 extends into the space between sensing element 14 and bore 26. A retaining ring 50 having a downwardly extending flange 52 about its periphery is positioned on flexible diaphragm 16. Flange 52 is received within flange 48 for holding flexible diaphragm 16 in contact with and centered on sensing element 14. The mechanical clamping force exerted by retaining ring 50 presses flexible diaphragm 16 against sensing element 14 and provides uniform contiguity of the abutting faces of flexible diaphragm 16 and sensing element 14. Partial separation of the abutting faces of flexible diaphragm 16 and sensing element 14 results in degradation of the accuracy of humidity indicator 10. Retaining ring 50 is composed of a metal such as steel or a plastic such as a polyamide resin.

An intermediate plate 54 formed with a cavity 56 at a lower surface and an opening 58 at an upper surface is inserted into cavity 22 and rests on flexible diaphragm 16. A hole 60 connects cavity 56 and opening 58. Cavity 56 constitutes a reservoir which is bounded by intermediate plate 54 and flexible diaphragm 16. Intermediate plate 54 is composed of a plastic, preferably a transparent plastic, such as acrylonitrile-butadiene-styrene or an acrylic.

A dial plate 62 having indicia 64 defining a scale of percent of relative humidity is superposed on intermediate plate 54. An "O" ring 66 is received within opening 58 and provides a seal between dial plate 62 and intermediate plate 54. Dial plate 62 is provided with a through hole 68, which is coaxially aligned with opening 58. Dial plate 62 is composed of a plastic such as acrylonitrile-butadiene-styrene or an acrylic and indicia 64 either is hot stamped, imprinted or silk screened thereon.

A cover plate 70, which is composed of a transparent plastic such as acrylonitrile-butadiene-styrene or an acrylic, is formed with a pair of interconnected grooves 72 and 74 that lie in the substantially spiral path. The diameter of groove 72 is approximately 0.92 inches and the diameter of groove 74 is approximately 1.48 inches, the width and depth of each groove being approximately 0.06 inches and 0.05 inches, respectively. A free end 76 of groove 72 extends radially inwardly and communicates with opening 58 in intermediate plate 54 through hole 68 in dial plate 62. A free end 78 of groove 74 extends radially outwardly and communicates with vent 35. Groove 74 communicates with the container interior through vent 35 so that when humidity indicator 10 is used with pressurized containers, there is no pressure differential across sensing element 14. Each groove 72 and 74 has a U-shaped profile in cross section and constitutes a capillary groove for transduction fluid 18. Capillary grooves 72 and 74 are formed by superposing dial plate 62 and cover plate 70 and bonding the plates together, free end 76 being aligned with hole 68.

After cover plate 70 and dial plate 62 are bonded together, capillary groove 72 is filled with a barrier fluid 80 such as glycerine and reservoir 56 is filled with transduction fluid 18 which is composed of mineral oil containing a dye, for example a blue dye. Then, the assemblage of cover plate 70 and dial plate 62 is bonded to housing 12. Screw 46, a fine thread screw, is turned into head 40 into contact with flexible diaphragm 16 and changes the volume of reservoir 56 for initial calibration of humidity indicator 10. The screw-diaphragm calibration arrangement provides great displacement per unit angle of screw rotation and high calibration sensitivity. As screw 46 is turned into head 40, transduction fluid 18 flows into capillary groove 72 and displaces barrier fluid 80 within capillary grooves 72, 74.

Figure 3:
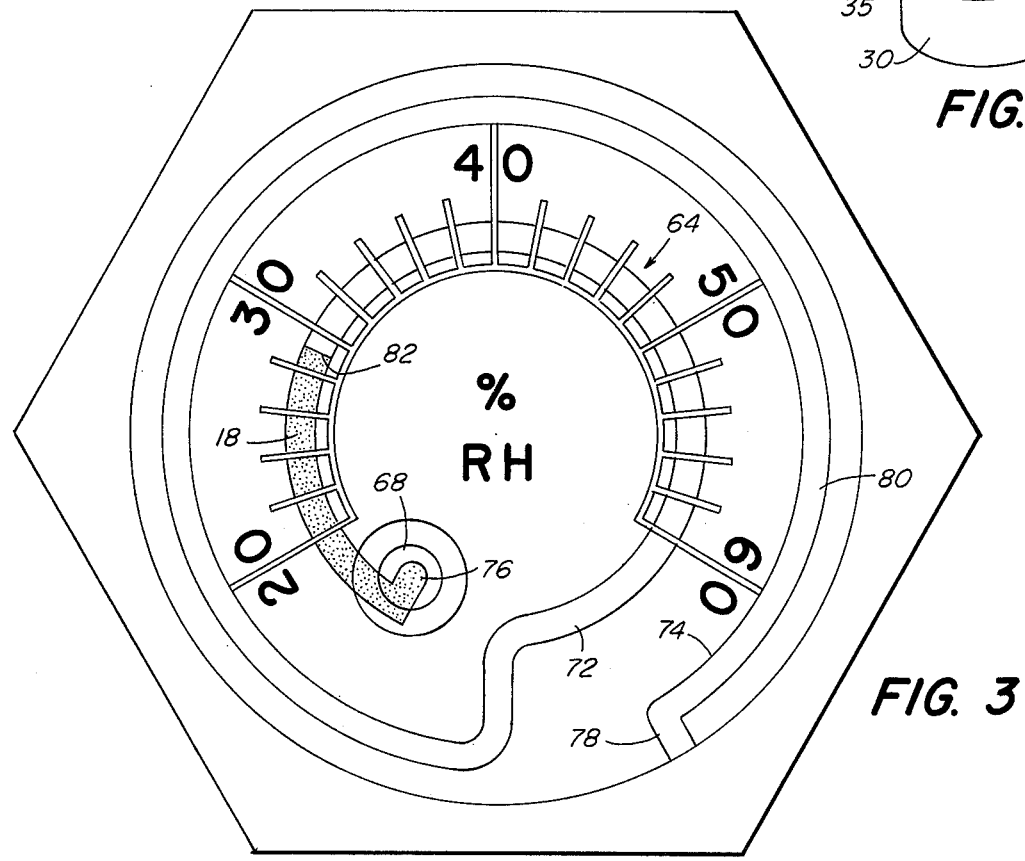
FIG. 3 is a top plan view of the humidity indicating device of FIG. 1.

As previously indicated, variation in the percent of relative humidity causes dimensional changes of sensing element 14, which, in turn, moves flexible diaphragm 16 and varies the volume of reservoir 56. As the volume of reservoir 56 changes, transduction fluid 18 and the barrier fluid 80 flow within capillary grooves 72, 74. The interface of the transduction fluid 18 and barrier fluid 80 at scale 64, depicted by reference character 82 in FIG. 3, indicates the percent of relative humidity. In the case of humidity readings above 60%, transduction fluid 18 and barrier fluid 80 flow into capillary groove 74 and do not overflow into housing 12. This arrangement prevents the formation of bubbles and voids in barrier fluid 80 which, if formed, would propagate into transduction fluid 18 and destroy the integrity of the capillary column.

The displaced volume $V_s$ of reservoir 56 equals the cross-sectional area of capillary grooves 72, 74 times the length of capillary grooves 72, 74 corresponding to a change from twenty to sixty percent relative humidity which is equal to the crown area of sensing element 14 times the length change of sensing element 14 for a change of relative humidity from 20 to 60 percent.

Humidity indicator 10 is designed to be insensitive to temperature change. When temperature increases at constant relative humidity, thermal expansion causes (1) an increase in the volume V of transduction fluid 18, (2) an increase in the length $l_s$ of sensing element 14, and (3) an increase in the length $l_h$ of housing 12. The increase in the volume of transduction fluid 18 and the length of sensing element 14 tend to increase the humidity reading, while the increase in the length of housing 12 tends to decrease the reading. Temperature compensation of humidity indicator 10 is provided by selecting material and dimensions such that the increase and decrease reading effects caused by thermal expansion cancel one another. For temperature compensation, the volume change $\Delta V_l$ of transduction fluid 18 due to thermal expansion plus the displaced volume $\Delta V_s$ of reservoir 56 due to sensing element 14 thermal expansion must equal the displaced volume $\Delta V_h$ of reservoir 56 due to housing 12 thermal expansion. That is, $$\Delta V_l + \Delta V_s = \Delta V_h$$

For a given temperature change $\Delta T$, the change in transduction fluid volume is:

$$\Delta V_l = V \alpha_l \Delta T$$

where V is the reservoir volume and $\alpha_l$ is the coefficient of thermal expansion of transduction fluid 18.

The displaced volume due to sensing element 14 expansion is:

$$\Delta V_s = \pi d_s^2 \Delta l_s / 4 = \pi d_s^2 l_s \alpha_s \Delta T / 4$$

Where $d_s$ is in the internal diameter of sensing element 14, $\Delta l_s$ is the change in sensing element 14 length and $\alpha_s$ is the coefficient of (linear) expansion of the sensing element material.

The displaced volume due to housing 12 expansion is:

$$\Delta V_h = \pi d_s^2 \Delta l_h / 4 = \pi d_s^2 l_h \alpha_h \Delta T1 / 4$$

where $\Delta l_h$ is the change in housing length and $\alpha_h$ is the coefficient of expansion of the housing material. Since $\Delta V_l = \Delta V_h - \Delta V_s$ and the reservoir volume is $\pi d_r^2 t/4$, t being the height of reservoir and $d_r$ the diameter of the reservoir which equals $d_s$, then $$t \alpha_l = \alpha_h l_h - \alpha_s l_s$$

Since $l_s$ is roughly equal to $l_h$, the above equation can be further simplified:

$$t/l_s = (\alpha_h - \alpha_s)/\alpha_l$$

This equation represents the fundamental equation for temperature compensation and relates the geometrical parameters of the design (t and $l_s$) to the material properties ($\alpha_l$, $\alpha_s$ and $\alpha_h$). Substituting numerical values of the expansion coefficients for transduction liquid 18 (Mineral oil; $\alpha_l = 90 \times 10^{-5}\,°C^{-1}$), the sensing element 14 (Nylon 6—6; $\alpha_s = 8 \times 10^{-5}\,°C^{-1}$), and housing 12 (ABS; $\alpha_h = 11 \times 10^{-5}\,°C^{-1}$), the reservoir height (t) is:

$$t = (11 \times 10^{-5} - 8 \times 10^{-5})/(90 \times 10^{-5}) = 0.034 l_s$$

Thus, for temperature compensation, the reservoir height is approximately 0.034 times the sensing element length.

Since certain changes may be made in the foregoing disclosure without departing from the scope of the invention herein involved, it is intended that all mattter contained in the above description and depicted in the accompanying drawings be construed in an illustrative and not in a limiting sense.

What is claimed is:

1. A humidity indicator comprising:
   (a) a housing formed with a cavity;
   (b) sensing element means constrained within said cavity for movement relative to said housing, said sensing element means composed of a material that changes dimensionally in response to humidity variations, said sensing element having a head that is formed with a through hole;
   (c) a flexible diaphragm captively held within said cavity in contact with said head;
   (d) an adjusting member received within said hole, said adjusting member configured to move said flexible diaphragm;
   (e) first plate means received within said cavity, said first plate means formed with an opening on one face thereof, said flexible diaphragm disposed between said head and said first plate means, a reservoir formed between said first plate means and said flexible diaphragm;
   (f) second plate means formed with a capillary groove, said first plate means and said second plate means formed with a port interconnecting said reservoir and said capillary groove; and
   (g) a transduction fluid within said reservoir constrained to flow within said capillary groove when the volume of said reservoir changes as a result of movement of said flexible diaphragm in response to dimensional changes in said sensing element due to variations in humidity.

2. The humidity indicator as claimed in claim 1 wherein said second plate means includes a cover plate and a dial plate, said cover plate formed with at least one groove to comprise said capillary groove, said dial plate having indicia in the form of a scale representing percent of relative humidity, said cover plate superposed on said dial plate for forming said capillary groove.

3. The humidity as claimed in claim 2 wherein said capillary groove is in the form of at least first and second interconnected grooves that lie in a substantially spiral path.

4. The humidity indicator as claimed in claim 3 wherein a free end of said first groove extends radially inward and a free end of said groove extends radially outward, said free end of said first groove aligned with said interconnecting port.

5. The humidity indicator as claimed in claim 1 wherein the composition of said housing, said sensing element and said tranduction fluid is such that the volume change of transduction fluid due to thermal expansion plus the displaced volume of said reservoir due to thermal expansion of said sensing element equals the displaced volume in said reservoir due to thermal expansion of said housing.

6. A humidity indicator comprising:
   (a) a housing formed with a cavity;
   (b) a sensing element received within said cavity, said sensing element composed of a material that changes dimensionally in response to humidity variations, said sensing element having a head that is formed with a through hole;
   (c) a flexible diaphragm received within said cavity in contact with said head;
   (d) retainer means for captively holding said flexible diaphragm against said sensing element and for providing contiguity of the abutting faces of said flexible diaphragm and said sensing element;
   (e) an adjusting member received within said hole, said adjusting member configured to move said flexible diaphragm;
   (f) an intermediate plate received within said cavity, said intermedite plate formed with an opening on one face thereof, said flexible diaphragm disposed between said head and said intermediate plate, a reservoir formed between said intermediate plate and said flexible diaphragm;
   (g) a cover plate formed with a groove on one face thereof;
   (h) a dial plate superimposed onto an affixed to said one said of said cover plate said dial plate sealing said groove and forming an open ended capillary tube, said intermediate plate and said dial plate formed with apertures defining an interconnecting port between said reservoir and one end of said capillary tube; and
   (i) a transduction fluid within said reservoir constrained to flow within said capillary tube when the volume of said reservoir changes as a result of movement of said flexible diaphragm in response to dimensional changes in said sensing element due to variations in humidity.

7. The humidity indicator as claimed in claim 6 wherein said groove formed in said cover plate is in the form of a pair of interconnected grooves that lie in a substantially spiral path.

8. The humidity indicator as claimed in claim 7 including a barrier fluid within said capillary tube in contact with said transduction fluid.

9. The humidity indicator as claimed in claim 8 wherein said dial plate includes indicia representing percent of relative humidity, said indicia disposed along one of said grooves, percent of relative humidity being indicated on said indicia at the interface of said transduction fluid and said barrier fluid.

10. The humidity indicator as claimed in claim 9 wherein said transduction fluid is composed of a mineral oil containing a dye and said barrier fluid is glycerine.

* * * * *